United States Patent
Hiromoto

(10) Patent No.: US 7,404,959 B2
(45) Date of Patent: *Jul. 29, 2008

(54) ENVIRONMENTALLY SAFE AGRICULTURAL SUPPLEMENT

(75) Inventor: Bryan Hiromoto, Honolulu, HI (US)

(73) Assignee: ABR, LLC, Puunene, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/757,961

(22) Filed: Jun. 4, 2007

(65) Prior Publication Data

US 2007/0232491 A1    Oct. 4, 2007

Related U.S. Application Data

(63) Continuation of application No. 10/622,026, filed on Jul. 16, 2003, now Pat. No. 7,270,823.

(60) Provisional application No. 60/396,833, filed on Jul. 16, 2002.

(51) Int. Cl.
*A61K 36/00* (2006.01)
*C12N 5/00* (2006.01)

(52) U.S. Cl. .................. 424/195.15; 435/420; 435/430

(58) Field of Classification Search ........................ None
See application file for complete search history.

(56) References Cited

U.S. PATENT DOCUMENTS

| 3,961,938 | A | | 6/1976 | Iizuka et al. |
| 5,714,658 | A | | 2/1998 | Heidlas et al. |
| 6,048,714 | A | | 4/2000 | Hiromoto |
| 6,090,615 | A | * | 7/2000 | Nagaoka ..................... 435/267 |
| 6,517,851 | B1 | * | 2/2003 | Hiromoto ..................... 424/405 |

FOREIGN PATENT DOCUMENTS

| GB | 1594227 | | 7/1981 |
| JP | 53069826 | * | 6/1978 |
| JP | 55045365 | | 3/1980 |
| JP | 2104278 | | 4/1990 |
| JP | 06062661 | * | 3/1994 |
| RU | 94038110 | | 2/1997 |
| RU | 2096449 | | 11/1997 |
| SU | 1526223 | | 4/1998 |
| WO | WO-00/65029 | | 11/2000 |

OTHER PUBLICATIONS

Brizuela et al., Revista Ibero Americana de Mycologgia (1998) 15:69-74 [English abstract].
Database WPI, AN 1978-54390A.
Database WPI, AN 1980-35225C.
Database WPI, AN 1990-161268.
Database WPI, AN 1994-114125.
Georgian Patent Office Search Report, for Georgian Patent Application No.: 8629/01-2005, 2 pages.
"Handbook of Applied Mycology," *Fungal Biotechnology* (1992) 4:588.
International Search Report for PCT/US03/22308, mailed on Feb. 11, 2004, 4 pages.
Kimura et al., Bioscience Biotech & Biochem. (1993) 57:687-688.
Supplementary European Search Report for EP 03 76 4773, mailed on Aug. 25, 2005, 4 pages.
Provisional Conclusion on non-patentability of the invention for Ukranian application No. 200501225, mailed Jun. 25, 2007, 3 pages.

* cited by examiner

*Primary Examiner*—Christopher R. Tate
(74) *Attorney, Agent, or Firm*—Morrison & Foerster LLP

(57) ABSTRACT

A substantially microbe-free composition containing plant growth regulators is produced by culturing a fungal spawn on high carbohydrate medium under suitable conditions. The culture filtrate is sterilized, formulated, and used to enhance plant growth.

21 Claims, No Drawings

ENVIRONMENTALLY SAFE AGRICULTURAL SUPPLEMENT

CROSS-REFERENCE TO RELATED APPLICATIONS

This application is a continuation of U.S. application Ser. No. 10/622,026, filed 16 Jul. 2003 which claims benefit under 35 U.S.C. § 119(e) to U.S. provisional application Ser. No. 60/396,833, filed 16 Jul. 2002, the contents of which are incorporated herein by reference.

TECHNICAL FIELD

The invention relates to a formulation which enhances growth and quality of food and ornamental crops. More specifically, the invention concerns a sterilized filtrate derived from composting high-sugar-content medium, preferably agricultural waste.

BACKGROUND ART

A wide variety of strategies has been used to enhance the productivity of food crops, including the use of fertilizers as nutritional supplements, application of pesticides to counteract the negative effect of infestation, and supplementation with growth hormones such as auxins and gibberellic acids. Each of these approaches, especially when implemented using synthetic materials, poses problems with respect to unacceptable alteration of the environment and concomitant unbalancing of the ecosystem.

It is understood that plant growth regulators are produced by some fungi. For example, gibberellins, indole-acetic acid, cytokinins, and other compounds useful in regulating plant growth are found in *Basidiomycetes* as reviewed by Brizuela, M. A., et al., *Revista Ibero Americana de Mycologgia* (1998) 15:69-74; the plant growth regulator dihydroampullicin is produced by a fungus *Ampulliferina* (Kimura, Y., et al., *Bioscience Biotech. & Biochem.* (1993) 57:687-688) and it is generally known that *Neurospora* and various phytopathogenic fungi produce plant growth regulators. It is also known that *Polyporus versicolor*, a white rot polypore produces plant growth regulators. However, culture conditions to enhance the production of plant growth factors vary widely.

*Basidiomycetes* have been shown to produce gibberellins, auxins, indoleacetic acid, abscisic acid, cytokinins and ethylene, as well as other plant stimulatory metabolites. The production of these factors, however, has been shown in the context either of production when in association with a plant per se, or on small-scale laboratory bases.

The present invention provides a method to provide plant growth factors from fungi, in particular *Basidiomycetes*, on a commercial scale. It has been generally considered not possible to do this. For example, according to "Handbook of Applied Mycology," Vol. 4, *Fungal Biotechnology* (1992) page 588

It is interesting to note that the species of Taphrina and Exobasidium formed yeasty like cells and spores in surface layers on the parasitized tissues of the host plant. When grown on submerged fermentation (SMF) process in synthetic media, the cytokinin (CK) production by these fungi was too small to cause extensive morphological changes that occur naturally in the host plant in spite of the growth in SMF medium in the form of yeast like cells. It was therefore stressed that the production of CK by pathogenic hyphal cells of Taphrina growing on host tissues was undoubtedly different in quantities. The close resemblance of the growth of the fungi under solid state fermentation technique to the above type of growth of the fungi on the host tissue is well known.

Further, according to this source,

It is obvious that the obligate parasitic, mycorrhizal, ascomycetous, and basidiomyceteous fungi have no potential in fermentative production of CK (cytokinin) due to problems in cultivation and slow growth rate.

Downstream processing involves handling of large volumes of liquid for separating extremely low quantities of GA3 (Gibberellic Acid 3), and thus is cost intensive when compared to other fermentation products such as citric or gluconic acids.

After separation of mycelial cells by filtration or centrifugation, GA3 is either adsorbed on suitable resins/adsorbents or extracted in appropriate solvents. Further purification involves a series of operations such as repeated liquid-liquid partitioning, concentration under vacuum, and final processing to obtain amorphorus powder or crystals of GA3.

Thus, even if it is known that certain plant parasitic fungi may produce plant growth regulators, the fungi may not produce the plant growth regulators (PGR) in quantity in fermentation systems to be of practical use unless culturing, extraction and concentration steps are taken.

It has now been found that an environmentally friendly stimulant of growth can be supplied by composting agricultural waste in the presence of fungal spawn, sterilizing the culture filtrate, and applying the resulting "liquid compost factor (LCF)" directly to field crops even after diluting with water 1 to 500 or up to 1:10,000. There is no need for extraction or chemical separation steps in order to obtain a useable solution. Only heating and filtration are needed. No solvents or resin beds are needed for extraction or concentration. The solids and filter material itself from filtration step of the heated liquid culture fluid may be dried and used as a source of plant growth stimulants as well. The dried material may be added to compost as an additive.

DISCLOSURE OF THE INVENTION

The invention is directed to a composition for stimulation of rapid root growth and plant bulk, as well as enhanced productivity in field crops, trees and other plants, which composition comprises the pasteurized culture filtrate of a fungal spawn grown, preferably on agricultural waste, but in any event, on medium with a high available carbohydrate concentration. The resulting "Liquid Compost Factor (LCF)" can be applied in a variety of ways to many crops to result in increased rates of growth and yields.

Thus, in one aspect, the invention is directed to a method to prepare a plant supplement, which method comprises culturing fungal spawn on a medium with at least 10% available carbohydrate concentration in the presence of light, and aeration under conditions whereby the mycelial mat is undisturbed, harvesting the culture, denaturing protein, removing solids, and pasteurizing or otherwise sterilizing the filtrate, to obtain said composition. In another aspect, the invention is directed to the composition prepared by this method. The invention composition thus comprises the sterilized culture filtrate of a fungal spawn culture grown in high carbohydrate medium, preferably comprising agricultural waste. In still another aspect, the invention is directed to methods to enhance plant growth and productivity using this composition, either alone or in combination with other growth promoters. Thus, the invention is also directed to methods to culture plants using the compositions of the invention whether the invention compositions are used alone or in combination with, for example, herbicides, insecticides, nematicides, or other growth stimulators or nutrients.

MODES OF CARRYING OUT THE INVENTION

The invention is directed to an environmentally friendly plant growth stimulating composition designated "Liquid Compost Factor (LCF)." LCF is the sterilized culture filtrate of a fungal spawn culture which has been grown under specified conditions and in a medium high in carbohydrate. The compositions of the invention include the sterilized filtrate from the fungal spawn as well as dried forms thereof and of recovered solids from filtration. Typically, either of these compositions is diluted in aqueous solution. The resulting diluted LCF, when applied to field crops such as corn, taro, lettuce, soy bean, cucumber, tomato, pineapple and other food crops, is able to stimulate root growth, enhance fruiting productivity, and improve crop yield. LCF has been shown to alleviate nematode infestation symptoms in established crops, and aids in disease reduction such as the reduction of fungal leaf spots, leaf rot and bacterial bulb rot. LCF may also be used on ornamental plants and is able to enhance flowering. It is effective on turf wherein it enhances greening. LCF can also be used to extend the life of cut flowers and foliage. LCF is also useful in enhancing tree growth thus, for example, assisting reforestation efforts.

The LCF of the invention contains plant growth regulators which are secondary metabolites of the fungal culture, as well as elicitors of plant defense mechanisms. The production of these plant growth regulators is effected by appropriate culturing conditions, by appropriate medium composition, and by proper post-culture treatment. The medium must contain sufficient available carbohydrate and sufficient potassium ion to effect this production with the appropriate precursors for metabolic production of the PGR's. Molasses contains about 2%-6% potassium and is a preferred, environmentally acceptable source, although other sources such as bananas, potatoes, prunes, oranges, tomatoes, artichokes, squash, grapes, sunflower, spinach, seeds or almonds could be used as well. The final concentration of $K^+$ should be 0.005% to 0.1% wt/vol., preferably 0.01%-0.1% wt/vol.

In general, the higher the available carbohydrate content, the more efficient the production of plant growth regulators; however, too high a concentration of carbohydrate in the form of sugars would unacceptably increase osmotic pressure and thus retard or eliminate growth of the fungus. Other factors which enhance the production of plant growth regulators in the ultimate product include growth under conditions of aeration under conditions wherein the mycelial mat is left undisturbed and in the presence of light predominantly in the long wavelength portion of the visible spectrum. The lighting conditions suitable for culture are preferably those derived from U.S. Pat. No. 5,123,203, the contents of which are incorporated herein by reference. By addition of carotenoid pigments and reduction of $Ca^{+2}$ in the fruiting substrates, red light sources were found to be preferred. Plant growth regulator (PGR) production is thus also enhanced by addition of carotene to the medium sufficient to produce a yellow color. If pineapple juice is employed as a carbohydrate source, sufficient carotene is inherently present.

The culture medium will contain an available sugar concentration corresponding to a content of 5-10% molasses. Although agricultural waste may be used to compose the medium, any source of suitable carbohydrates and other required nutrients, including carotene, could be used; some portion of the nutrients may be supplied by the fungal spawn itself which is prepared by culturing fungi in the presence of grains and other nutrients. Thus, the required sugar content of the medium can be supplied by syrups prepared from any source, including various fruits, corn syrup, sugar cane syrup, sugar beet syrup, molasses, and the like. Syrups prepared from other fruits, such as pineapple, orange, plum, grape, papaya and many other may also be used. It is preferred to use plant extracts as a source of nutrients in the medium.

The medium must have an available carbohydrate content which is higher than that typical for culturing of fungi. By "available carbohydrate" is meant carbohydrate energy sources which are metabolizeable by the fungal culture. Typical components of these available carbohydrate include sucrose, glucose, other simple sugars and disaccharides. Typically, the medium will contain at least 10% wt/vol available carbohydrate, preferably 12% wt/vol, more preferably 13% wt/vol, and even more preferably 15% wt/vol. Alternatively, the final concentration in the medium results in a BRIC reading of at least 10, more preferably at least 12, most preferably at least 15. High concentrations of available carbohydrate are highly preferred and, as stated above, are limited only by the necessity to avoid generating unacceptable osmotic pressure conditions. Since fungi are able to digest cellulose, enhancing the carbohydrate levels in the form of cellulose, or other carbohydrate which does not enhance osmotic pressure, may preferably be used.

It appears that optimal BRIC values for the culture medium are in the range of 12-15. In one typical culture, BRIC values above 19, e.g., 24 or 30, resulted in either very slow growth or no growth at all. At 19 BRIC, the mycelial covered the surface of the medium but in only a thin layer; at 11 BRIC and 8 BRIC a very good growth is achieved. However, at below 11 BRIC, the PGR content appeared to be less.

In addition to the available carbohydrate as a carbon source, the medium must also contain other nutrients, notably a source of nitrogen and various cofactors. Typically, there is sufficient source of most of these nutrients in the fungal spawn used for an inoculum. However, it appears important that the medium contain a concentration of carotene which is sufficient to provide a visible yellow color.

If molasses is used as at least a portion of the source for available carbohydrate, the molasses itself supplies many vitamins and other nutrients required by the fungus. Syrups prepared from sugar cane are preferred to those prepared from sugar beet as these syrups provide a better source of nutrients. Other sources of desirable nutrients include the use of bananas for supply of potassium ion and papaya is also a helpful addition to the medium. Papaya contains carotenoids, sugars, and sulfur compounds. It is particularly high in fructose.

The medium is first sterilized, preferably by heating to a sufficient temperature for a sufficient time to remove any contaminating organisms. The decontaminated medium is then inoculated with a culture of fungus, i.e., a fungal spawn.

Any fungus can be used in the invention provided it is adaptable to the culture techniques described herein. While a multiplicity of fungi have been described as able to produce plant growth regulators, typically, this has not been the case as a means for commercial or practical production of these compounds.

The culturing of fungi useable to obtain the LCF compositions of the invention can be conducted in an efficient manner using readily available equipment. While stainless steel drums are useful, they are expensive and unless the stainless steel is especially formulated to resist corrosion, corrosion may occur during fermentation. Glass or plastic containers are therefore preferred. It has been found particularly convenient to culture the fungi in 55 gallon translucent plastic drums with just a cotton plug in the spigot. The insides of the drums or other containers are first decontaminated, for example with a dilute iodine solution, prior to use.

The preferred fungi useful in the invention are *Basidiomycetes*—i.e., a class of fungi that coexist with, and depend for growth on, plants in nature. *Basidiomycetes* can be porous or gilled and preferred sources for the spawns cultured in the method of the invention are the porous fungi, in particular those of the family *Polyporaceae*. The *Polyporaceae* can generally be classified as constituting genera that are brown rot fungi or white rot fungi. The brown rot fungi degrade the white cellulose in wood on which they grow, thus leaving the brown lignin behind; the white rot fungi do the opposite— they degrade the lignin and leave the white cellulose behind. Thus, preferred fungi for use in the method of the invention are brown rot *Polyporus* fungi, and in particular those of the genera *Bridgeoporus, Ceriporia, Daedalea, Laetiporus, Oligoporus*, and *Pycnoporellus*.

Thus, the invention can employ, in the specific culture conditions required, various members of the *Basidiomycete* class, but preferably those that are in the *Polyporus* family and in particular those that are of the brown rot type.

A particularly preferred fungus for use in the invention is *Laetiporus*, especially *Laetiporus sulphureus*. *Laetiporus sulphureus* "Sulphur shelf" or "Chicken of the Woods" is a wound parasite of hardwood trees. It is commonly found in Hawaii on Eucalyptus robusta. Since this fungus lives in the heart wood of the tree, it is not noticeable on the outside of the tree. The fruiting body or mushroom appears as a sulphur or orange color bracket mushroom appearing every few years. The fungi feed on the heartwood and produce a cubical brown rot internally since the lignin is left after the cellulose and hemicellulose have been dissolved by enzymatic action. Tree death occurs many years after infection has started. The ability of this fungus to control the growth of the host tree was not noticed in published literature nor has any plant stimulatory material been associated with this fungus. In controlled fungal liquid culture growth of the present invention, these plant growth factors have been produced in large quantities and have been demonstrated to affect plant growth in plants outside the usual host range. As described herein, in order to utilize the plant stimulatory material, the tissue degradation enzymes are destroyed by heating the fluid; the stimulatory material is heat stable at 100° C.

The fungal liquid culture of *L. sulphureus* has been shown to stimulate seed germination of corn, soybeans, lettuce, beans, grains and grasses; foliar spray has been shown to affect pineapples, coffee, tomato, taro, sugarcane and other crops. This fungus normally affects the growth of an 100 ft tall eucalyptus tree weighing tons of biomass. The plant stimulatory effect is effective on smaller plants as well, with the proper dilution. The liquid culture fluid can be diluted 1:3,000, for example, with water and still be effective. In nature, *Laetiporus* fungi have balanced the various plant growth regulators production in order to stimulate a large host tree with massive girth and root system. This balance is applied on smaller plants and trees with desirable effects.

The fungal spawn is thus comprised preferably of a *Basidiomycete*, more preferably of a brown rot *Basidiomycete*, and more preferably a *Laetiporus* fungus, grown under suitable conditions for the particular choice of fungal organism. The nutrient medium for the fungus contains suitable components that are specifically tailored to the fungus employed, but must always contain, of course, a source of carbon, a source of nitrogen, and relevant vitamins and cofactors. The spawn is produced by culturing for a suitable time period sufficient to provide sufficient fungal inoculum so that a mycelial mat will be formed in the culture medium of the invention. Typical time for formation of the spawn from an initial inoculation range from 5 days-100 days.

A commercially available liquid fungal spawn useful in the invention may be obtained from Kukui Spawn Co., formerly Maui Shiitake Trading Company, both of Maui.

The liquid spawn is then used to inoculate the culture medium for preparation of the LCF. The inoculated culture medium is cultured without agitation in the presence of light predominantly in the long wavelength portion of the visible spectrum, at a temperature of 15-37° C., preferably about 20° C. for a sufficient time to generate the required levels of PGR. Typically, PGR are produced in useful quantities after 30 days of culture, preferably after 45 days, and more preferably after 60 days.

Although agitation of the inoculated culture medium is to be avoided in order to avoid disturbing the mycelial mat, aeration of the medium may be desired. This can be supplied, for example, by bubbling oxygen through the medium, or other means whereby the mycelial mat is left undisturbed. It has been found that sufficient oxygen is available even without bubbling air through the medium and simply permitting aeration to occur through interaction with the mycelial surface.

By "long wavelength portion of the visible spectrum" is meant light with a wavelength of approximately 500-800 nm, preferably 600-750 nm. Other wavelengths may be included, but the predominant wavelengths should be in the above range. Thus, as a percentage of total photons, the long wavelength portion should represent more than 50% of said photons.

PGR levels can be assessed using standard bioassay methods. Comparison of soybean bean seedling growth at known concentrations of LCF used as a soil drench in potting soil are used as growth standards. The color of the LCF solution correlates to efficacy on soybean seedlings over time. Fertilizer rates have been set for both treated and control and seedlings are evaluated 14 days after application. Effects of differences in total weight, root weight, root length, foliage weight, and height are measured for comparison with effects from Standard LCF solutions. Alternatively, the color of the culture fluids can be used as an index as it has been found that a color change from yellow to deep wine red is correlated with the production of PGR.

The strength of a LCF solution is controlled by matching the color of a known LCF solution "Standard" that has a useable dilution strength of 1:500 on soybean seedlings. Usually a culture that has been incubating for 60 days will be diluted with water 1:2 to reach a color intensity of that will match the Standard. Longer incubation time leads to further dilution of the culture fluids to reach the Standard LCF levels.

As the culture matures, a mycelial mat will be grown, and the liquid portion of the culture can readily be removed aseptically when sufficient PGR production has occurred. Solids are removed from the harvested culture medium, preferably by filtration or alternatively by centrifugation or other known means to separate out solids. The liquid portion is then subjected to heating to 100° C. and held for 10 minutes. This step denatures the enzymes such as cellulase, lipase and hemicellulases. Chemical/temperature protein extractions or membrane filtration could also be used. The denatured proteins can then be paper filtered or removed by centrifugation. The liquid portion is then subjected to suitable sterilization procedures, such as pasteurization and ultrafiltration, preferably pasteurization. The resulting pasteurized "LCF" is then packaged in sterile containers. The culture flask with the mycelial mat is then, if desired, refilled with sterile, cool nutrient solution for preparation of additional LCF. The first LCF production takes 60 days, the second requires only about 30 days since the mycelial mat has been established in the first run. The third and subsequent production runs are 30 days long and may be continued until the culture vessel becomes contaminated.

By "culture filtrate" is meant the liquid portion of the culture described. "Culture filtrate" is a commonly used term, despite the fact that recovery of this filtrate may not necessarily be effected by actual filtration. Indeed, in many of the cultures of the present invention, a mycelial mat is formed so that the culture filtrate may be removed by decanting or by siphoning. "Culture filtrate" thus refers simply to the liquid portion of the culture.

"Sterilization" of the LCF of the invention can be effected by a variety of means. Because pasteurization is the most practical, the composition is referred to as LCF. However, other modes of sterilization could also be effected, such as ultrafiltration or inclusion of antibiotics or sanitizers such as Idophor.

In addition to the sterilized culture filtrate, the LCF compositions of the invention also include the material retained upon filtration of the culture which can be dried. This material also contains PGR and can be used in a manner similar to the sterilized filtrate.

The mycelial mat can be reused after removal of the medium for harvesting the LCF. Typically, the medium can be removed through tubing from under the mat and replaced by new sterile medium. As typically the mat is broken during removal of the prior medium, the new sterile medium can simply re-poured into the container and the portions of the mat re-assemble and continue to grow.

In addition to the production of plant growth regulators according to the methods of the invention, it has been found that the medium contains, as well, elicitors of materials which constitute the defenses of plants against pathogens. These defense mechanisms, known generally as phytoalexins are engendered in plants which are infected with parasites or pathogens. A general discussion of these mechanisms is found in the report of a lecture entitled "How Plants Defend Themselves Against Pathogens," Lecture 8 from U. of Idaho Plant Science 405/504 courses found at www.uidaho.edu/ag/plantdisease. As outlined, in general, structural defenses involve, for example, formation of waxes, cork layers, abscission layers, and the like which constitute barriers for disruption of plant metabolism. Metabolic defenses include preexisting defenses as well as those elicited by the infection with pathogens. These defenses include production of the toxic substances designated as phytoalexins. The LCF of the invention is able to elicit responses of this type.

Thus, one aspect of the invention combines the plant growth regulation effects of the LCF with eliciting production of phytoalexins. This aspect can be strengthened by addition of known phytoalexin inhibitors, such as the product called Messenger containing the protein Harpin, manufactured by Eden Bioscience.

The LCF is diluted to a suitable concentration for application to crops or trees. Dilutions of 1:100-1:2,000 or 1:5,000 can be used, depending on the concentration of PGR and the desired effects. The level of dilution depends, of course, on the initial concentration of the PGR, the manner in which the material is to be applied, and a number of other factors that are well within ordinary skill to determine. LCF dilutions as high as 1:6,000 or even greater degrees of dilutions 1:10,000, have been found effective in many cases. The LCF may also be dried on an inert support such as talc or diatomaceous earth for application, or may be dried onto a granular fertilizer to boost the performance of the fertilizer. In general, the diluted LCF may be applied in any conventional manner, such as including in a planting dip or foliar spray, adding through drip irrigation systems, mixing with potting soil, applying to surrounding soil for seedlings, etc.

In one embodiment application rates are 6-8 oz of LCF per 30 gal of water per acre when used as a spray or soil supplement. However, applications of larger amounts of a liquid are preferred. Preferably, the total liquid applied to an acre will be 100-500 gallons with the dilution approximating 1 pint-1.5 quarts diluted to 100-200 gallons water. Thus, typical applications would use 1 quart of LCF as sterilized medium in 125-200 gallons of water per acre applied as a spray or 2 quarts of the sterilized culture filtrate LCF diluted in 325 gallons of water per acre.

However, as stated above, the culture filtrate LCF may also be dried unto a granular substance and applied as a dried material.

The LCF and its dilutions or other formulations can also be mixed with other acidic materials such as pesticides, other nutrients and/or fertilizers for combined application. Mixing with basic fertilizers or solutions should be avoided. A particularly preferred mixture is that with the surfactant blend crop adjuvants described in PCT publication WO 96/38590, which is incorporated herein by reference. Alternatively, nematicide mixtures which consist entirely of exempt ingredients, such as mixtures of sodium lauryl sulfate, molasses, safflower oil and cheese could also be used. These are described in copending application 60/390,289, filed 21 Jun. 2002 and incorporated herein by reference. As stated above, also included in the formulation may be elicitors of the phytoalexin defense proteins or metabolites.

By way of illustration, the LCF can be supplied as a 1% (wt/wt) coating on fertilizer pellets designed for turf grass or for vegetables and trees. A 2% (wt/wt) coating on diatomaceous earth is a suitable seed treatment flour for small seeds such as lettuce, tomato, cabbage and eggplants; higher percentages of LCF coated on diatomaceous earth are useful for larger seeds. For example, a 6.5% coating is suitable for corn, beans, soybeans, peas and cucumbers. Bare root seedlings, corms, pineapple crowns, and other vegetative planting material can be dusted with this flour to enhance growth.

A convenient mode of application is to add about ½ teaspoon of the flour to an ounce of seed in a plastic bag. After closing the bag, the bag is shaken to coat the seeds with flour, the excess flour is recovered and the resulting seeds have a fine coat of the flour.

In general, the LCF should be stored at room temperature, out of direct sunlight, under dry conditions. While the LCF is environmentally safe, it should not be ingested and should not be allowed to remain on the skin for extended periods.

The following examples are intended to illustrate but not to limit the invention.

EXAMPLE 1

Preparation of Pasteurized LCF

Medium was prepared from:
20 gal of high-fiber pineapple juice retentate obtained from ultrafiltration,
1 gal of pineapple syrup,
20 gal of molasses water (5 gal of molasses mixed with 40 gals of water), and
5 gal of soft ripe-stage papaya purée, optionally including skin, seeds and pulp.

The total volume was then adjusted to 50 gal with additional retentate and/or molasses water. The components were mixed in an open plastic drum and transferred to stainless steel pots, brought to a boil, and held at 100° C. for at least 30 min. The hot slurry was transferred to a sanitized, white translucent, 55 gal plastic bioprocessing drum and cooled to room temperature. Cooling takes several days.

The cooled medium was inoculated with fungal starter culture (see below) under a laminar flow-hood and one or two sterilized cotton plugs were installed in the 55 gal drum. The drum was then incubated in an air-conditioned, lighted room for 60 days undisturbed. The lighting was supplied by Agrolights or deluxe warm white light. Cool white light is not satisfactory.

After 60 days, the liquid portion of the culture was removed and filtered to remove solids. The filtered liquid was heated to 100° C. for 10 minutes to denature soluble proteins. The heated medium was then filtered and reheated to 100° C. for 30 minutes to pasteurize. The pasteurized product was filled into sanitized bottles and kept at room temperature for storage. The pH of the LCF prepared in this Example is 2.5.

The fungal starter culture used in this Example was obtained from Kukui Spawn Co., formerly Maui Shiitake Trading Company, Hawaii. The entire 1 liter container of liquid spawn is added aseptically to the bioprocessing drum of cooled nutrient solution. Usually two bottles of spawn liquid culture is added per 50 gallon bioprocessing drum.

EXAMPLE 2

Application to Plants

One ounce of LCF as prepared in Example 1 was diluted into 5 gal of water. This mixture was applied to soil around coffee trees.

One ounce of LCF was diluted into 5 gal of water and used to treat corn plants, which grew 60% more bulk than control plants. Improved results were shown with dilution of 1 oz LCF to 10 gal of water.

A similar dilution of 1 oz LCF to 5 gal of water was used to spray Manoa lettuce which yielded 50% more leaf weight than controls.

Cucumber seeds were treated with 6.5% LCF flour prior to planting and the plants grew 39% heavier than controls.

One ounce of LCF diluted to 5 gal of water was applied to pineapple crowns and resulted in faster growing pineapples; improved growth results were also observed when older plants were foliarly sprayed with this dilution or when 3-year-old pineapple plants were dipped in this dilution.

A dilution of 1 oz LCF in 1 gal of water was used as a corm/planting dip for dry land taro, sweet potatoes and yams.

Taro seedlings grew 160% heavier than control plants in six weeks as a result.

In application to sugar cane, the dilution required varied with variety of plant. In some instances, 1 oz of LCF and 2½ gal of water was successful in obtaining 50% increase in shoot diameter.

Turf grass was made to grow at a faster rate by spraying with 1 oz LCF diluted in 5 gal of water.

LCF has also been used as a soil drench of 29 mls of a 1:500 dilution per seedling pot to treat Douglas fir, resulting in 10%-20% growth within four weeks.

LCF can be mixed with polymers for a dry seed coating treatments of grains, vegetables and other crops. Percentage LCF will vary with the crop.

LCF can be used to alleviate nematode infestation symptoms. A 1:500 dilution of 5 gallons per infested coffee tree.

Three applications in 5 months will increase roots, foliage branches, increase fruit uniformity and increase production.

LCF may be used to reduce plant disease incidences such as fungal leaf spots and bacterial rot of plants. Onion Bulb Rot may be reduced with a 1:1600 dilution of LCF applied foliarly every three weeks.

A weak solution of LCF, 0.1% solution may be used to extend the life of cut flowers, foliage and Christmas trees.

LCF may be used to reduce frost, insect and chemical damage to plants with a 1:500 foliar or soil drench application.

Pineapple shoots were tested by dipping shoots in a solution containing 800, 1000, or 2000 parts per million of the LCF sterilized culture filtrate for 10 minutes prior to planting in potting soil with granular fertilizer. The shoots were also dipped in a microemulsion surfactant blend nematicide at the same time. While the controls had an average root weight of 6.9 grams and an average root length of 29.4 inches, the 800 part per million LCF treated plants had root weights of 8.2 grams and root lengths of 33.35 inches; those treated with 1000 parts per million LCF showed root weights of 7.4 grams and root lengths of 41.4 inches, a 41% increase over control. However at 2000 parts per million, toxic effects appeared and the root weights and lengths were less than controls.

Garbanzo beans were soaked in a dilution of the sterilized culture filtrate LCF diluted 1 ounce in ½ gallon or 1 gallon of water. The beans were treated at a ratio of 1 ml of the diluted material per 100 grams of beans. The beans were then dried and planted and showed an increase of 22% in the yield of beans harvested as compared to untreated controls.

In other applications, the LCF composition treatments of the invention were combined with treatments with flower stimulators, herbicides, and turf grass growth inhibitors.

An increased fruit weight of 56% was obtained when LCF was applied to tomatoes.

The invention claimed is:

1. A composition which consists essentially of a sterilized culture filtrate recovered from a culture of the spawn of a *Basidiomycete* fungus incubated in a medium containing at least 10% available carbohydrate in the presence of long wavelength light, and in the substantial absence of agitation,
   wherein said medium has a BRIX value of 12-15 and further contains potassium ion and carotene, and
   wherein said filtrate is the liquid portion of said culture from which proteins have been denatured and removed, and
   wherein the filtrate has optionally been dried.

2. The composition of claim 1, wherein said medium comprises molasses and/or pineapple or papaya syrup or juice.

3. The composition of claim 1, wherein said medium contains sufficient carotene to impart a yellow color, and $K^+$ of 0.01%-0.1% wt/vol.

4. The composition of claim 1, wherein the *Basidiomycete* is a *Polyporus* fungus.

5. The composition of claim 4, wherein the *Polyporus* is a brown rot *Polyporus*.

6. The composition of claim 5, wherein the brown rot *Polyporus* is a *Laetiporus*.

7. A formulation for application to enhance plant growth and/or development which formulation comprises an effective amount of the composition of claim 1.

8. The formulation of claim 7 which comprises diatomaceous earth or fertilizer particles coated with said composition.

9. The formulation of claim 7, which further contains at least one pesticide and/or at least one nutrient and/or at least one herbicide.

10. The formulation of claim 7, which further contains at least one elicitor of phytoalexin production.

11. A method to enhance plant growth, development or bulk, which method comprises contacting the seeds or at least a portion of said plant with the formulation of claim 7.

12. The method of claim 11 which further comprises contacting the seeds or at least a portion of said plant with at least one pesticide and/or at least one nutrient and/or at least one herbicide.

13. A method for preparing a composition containing plant growth regulators, which method comprises culturing the spawn of a *Basidiomycete* fungus in a medium containing at least 10% available carbohydrate in the presence of long wavelength light and in the substantial absence of agitation, wherein said medium has a BRIX value of 12-15 further contains potassium ion and carotene;

recovering a culture filtrate;

denaturing soluble proteins in the filtrate and removing said denatured proteins; and sterilizing the remaining culture filtrate, and optionally drying said filtrate to obtain said composition.

14. The method of claim 13, wherein the medium contains sufficient carotene to impart a yellow color, and $K^+$ of 0.01%-0.1% wt/vol.

15. The method of claim 13, which said culture filtrate is recovered by filtering said culture.

16. The method of claim 13, wherein said denatured proteins are removed by filtering.

17. The method of claim 13, wherein said sterilizing is by pasteurization.

18. The method of claim 13, wherein the *Basidiomycete* is a *Polyporus* fungus.

19. The method of claim 18, wherein the *Polyporus* is a brown rot *Polyporus*.

20. The method of claim 19, wherein the brown rot *Polyporus* is a *Laetiporus*.

21. The method of claim 13 wherein the filtrate is dried.

* * * * *